(12) United States Patent
Goldstein et al.

(10) Patent No.: US 11,660,416 B2
(45) Date of Patent: *May 30, 2023

(54) METHODS OF ADMINISTERING HIGH CONCENTRATIONS OF NITRIC OXIDE

(71) Applicant: Mallinckrodt Hospital Products IP Limited, Mulhuddart (IE)

(72) Inventors: Brahm Goldstein, Chalfont, PA (US); Douglas Stuart Greene, Newtown, PA (US)

(73) Assignee: Mallinckrodt Hospital Products IP Limited, Dublin (IE)

(*) Notice: Subject to any disclaimer, the term of this patent is extended or adjusted under 35 U.S.C. 154(b) by 388 days.

This patent is subject to a terminal disclaimer.

(21) Appl. No.: 16/785,983

(22) Filed: Feb. 10, 2020

(65) Prior Publication Data

US 2020/0171264 A1 Jun. 4, 2020

Related U.S. Application Data

(63) Continuation of application No. 13/827,240, filed on Mar. 14, 2013, now Pat. No. 10,556,086, which is a continuation-in-part of application No. 13/420,852, filed on Mar. 15, 2012, now abandoned.

(51) Int. Cl.
| | | |
|---|---|---|
| *A61M 16/12* | (2006.01) | |
| *A61K 33/00* | (2006.01) | |
| *A61M 16/00* | (2006.01) | |
| A61M 16/20 | (2006.01) | |
| A61M 16/06 | (2006.01) | |

(52) U.S. Cl.
CPC ............ *A61M 16/12* (2013.01); *A61K 33/00* (2013.01); *A61M 16/024* (2017.08); *A61M 16/06* (2013.01); *A61M 16/202* (2014.02); *A61M 2016/0021* (2013.01); *A61M 2016/0027* (2013.01); *A61M 2016/0039* (2013.01); *A61M 2202/0275* (2013.01); *A61M 2205/3334* (2013.01); *A61M 2205/50* (2013.01); *A61M 2205/502* (2013.01)

(58) Field of Classification Search
CPC .................... A61M 2202/0275; A61M 16/04
See application file for complete search history.

(56) References Cited

U.S. PATENT DOCUMENTS

| | | | | |
|---|---|---|---|---|
| 2007/0104653 A1* | 5/2007 | Miller | ................... | A61K 9/007 424/45 |
| 2008/0029093 A1* | 2/2008 | Stenzler | ................ | A61K 33/00 128/203.12 |
| 2010/0089392 A1* | 4/2010 | Fine | .................... | A61M 15/008 128/203.29 |

* cited by examiner

*Primary Examiner* — LaToya M Louis
(74) *Attorney, Agent, or Firm* — Servilla Whitney LLC

(57) ABSTRACT

Described are methods of administering therapeutic gases comprising high concentrations of nitric oxide, particularly concentrations above 2,000 ppm. The therapeutic gas may be administered at a certain dosing rate, such as less than 166 micrograms of nitric oxide per second. Also described are methods of administering a therapeutic gas comprising nitric oxide to a patient, wherein a dose of nitric oxide is administered from a portable device that includes a delivery system and a mini-cylinder. Methods of intermittent administration of nitric oxide pulses are also described.

20 Claims, 1 Drawing Sheet

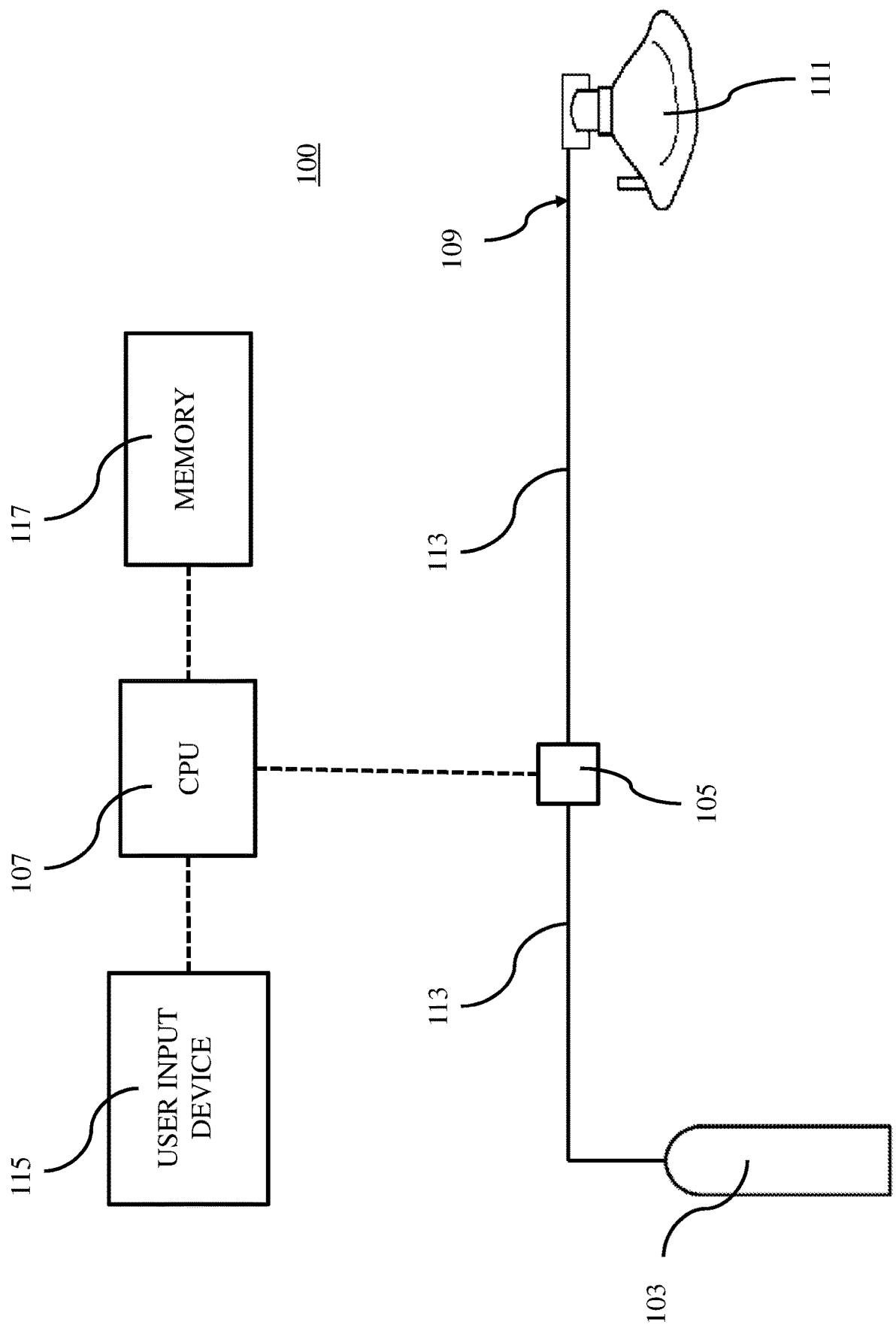

METHODS OF ADMINISTERING HIGH CONCENTRATIONS OF NITRIC OXIDE

CROSS-REFERENCE TO RELATED APPLICATIONS

This application is a continuation under 35 U.S.C. § 120 of U.S. patent application Ser. No. 13/827,240, filed Mar. 14, 2013, which is a continuation-in-part under 35 U.S.C. § 120 of U.S. patent application Ser. No. 13/420,852, filed Mar. 15, 2012, now abandoned, the entire disclosures of which is hereby incorporated by reference herein.

TECHNICAL FIELD

Embodiments of the present invention generally relate to the field of methods and devices for nitric oxide delivery.

BACKGROUND

Nitric oxide (NO) is a gas that, when inhaled, acts to dilate blood vessels in the lungs and reduces pulmonary hypertension. Because of this, nitric oxide is provided as a therapeutic gas in the inspiratory breathing gases for patients with pulmonary hypertension.

Current methods of nitric oxide delivery generally require that low concentrations of nitric oxide be delivered to a patient as high NO delivery concentrations are associated with various toxicities. Therefore, as a result, nitric oxide delivery systems require either the use of cylinders with low NO concentration, or if high concentration cylinders are used, require dilution of the NO prior to administration to the patient. If cylinders with low NO concentration are used, then the cylinders need to have a large volume in order to have a sufficient quantity of NO so that the cylinders do not need to be frequently replaced. Such large cylinders reduce the portability of the nitric oxide delivery system and make it less suitable for home use.

Therefore, there is a need to provide alternative methods of nitric oxide delivery that enable portable nitric oxide delivery systems that are convenient for home use.

SUMMARY

One aspect of the present invention provides a method of delivering nitric oxide to a patient, the method comprising administering a dose of nitric oxide at a delivery concentration of greater than 2,000 ppm. The dose of nitric oxide may be administered at a certain dosing rate, such as less than 200 micrograms of nitric oxide per second (µg NO/sec). In various embodiments, the dosing rate may be less than or equal to 200, 175, 166, 150, 125, 100, 95, 90, 85, 83, 80, 75, 70, 65, 60, 55, or 50 µg NO/sec.

According to one or more embodiments of this aspect, the dose of nitric oxide is administered during inspiration.

In certain embodiments, the nitric oxide is administered as a "pulse" or "bolus." Other embodiments provide that the nitric oxide is administered continuously.

Some embodiments provide that the nitric oxide is administered every nth breath, wherein n is 1 or greater. According to one or more embodiments, n is 1 such that the dose is administered every breath. In other embodiments, n is greater than 1 such that the dose is intermittent. Intermittent administration may also include skipping breaths randomly or if the dose to be administered in a given breath is lower than a threshold amount that may be delivered by the nitric oxide delivery device.

In one or more embodiments, the delivery concentration is in the range of 2,000 ppm to 20,000 ppm. In some embodiments, the delivery concentration is in the range of 2,200 ppm to 5,000 ppm.

According to one or more embodiments, the dose is in the range of 0.001 to 4.5 mg/kg/hr.

In one or more embodiments, the nitric oxide is administered in undiluted form such that the delivery concentration is the same as a storage concentration.

The nitric oxide administration may be part of a treatment of the various diseases described herein, such as pulmonary hypertension. In some embodiments, the pulmonary hypertension is pulmonary arterial hypertension (PAH) or is associated with chronic obstructive pulmonary disease (COPD).

Another aspect of the present invention relates to a method of administering a therapeutic gas comprising nitric oxide to a patient, the method comprising administering a dose of nitric oxide from a device that comprises a delivery system and a cylinder having a nitric oxide concentration greater than 2,000 ppm, wherein the nitric oxide is administered in undiluted form from the cylinder.

In one or more embodiments of this aspect, the nitric oxide is administered every nth breath, wherein n is 1 or greater. In some embodiments, n is 1 such that the dose is administered every breath. In other embodiments, n is greater than 1 such that the dose is intermittent.

In certain embodiments, the delivery concentration of the dose is in the range of about 2,000 ppm to about 10,000 ppm. In some embodiments, the delivery concentration is in the range of 2,200 ppm to 5,000 ppm. In a particular embodiment, the delivery concentration is in the range of 4,600 ppm to 5,000 ppm.

The cylinder that supplies the nitric oxide may be a "mini-cylinder." In one or more embodiments, the cylinder has a volume in the range of 0.01 to 1 L. According to some embodiments, the cylinder volume is in the range of 0.05 to 0.5 L.

According to one or more embodiments of this aspect, the dose is in the range of 0.001 to 4.5 mg/kg/hr.

Another aspect of the present invention pertains to a method of reducing the nasal irritation of a patient during nitric oxide administration. In various embodiments, the nitric oxide dosing rate does not exceed a certain rate to reduce the incidence of nasal irritation. The dosing rate may be any of the dosing rates described herein, such as less than or equal to 200, 166, 100 or 83 µg NO/sec.

Yet another aspect of the present invention provides a method of treating pulmonary hypertension comprising administering a therapeutic gas comprising a dose of nitric oxide to a patient from a device that comprises a delivery system and a cylinder, wherein the dose has a delivery concentration of greater than 2,000 ppm. In one or more embodiments, the nitric oxide is administered every nth breath, wherein n is 1 or greater.

In some embodiments of this aspect, the dose is in the range of 0.001 to 4.5 mg/kg/hr.

According to one or more embodiments, the nitric oxide is administered in undiluted form such that the delivery concentration is the same as a storage concentration.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

BRIEF DESCRIPTION OF THE DRAWING

So that the manner in which the above recited features of the present invention can be understood in detail, a more particular description of the invention, briefly summarized above, may be had by reference to embodiments, some of which are illustrated in the appended drawing. It is to be noted, however, that the appended drawing illustrates only typical embodiments of this invention and are therefore not to be considered limiting of its scope, for the invention may admit to other equally effective embodiments.

FIG. 1 shows a nitric oxide delivery system that can be used in accordance with one or more embodiments of the invention.

DETAILED DESCRIPTION

Nitric oxide (NO) is typically supplied from cylinders that contain up to about 1000 ppm NO in a carrier gas, such as nitrogen. Embodiments of the present invention use NO in a carrier gas, the NO having a concentration of 2,000 ppm or more (e.g., up to 5,000 or even 30,000 ppm), where a volume of gas from the source is controlled to deliver dosing of the NO using either a constant concentration, pulsed or other method of NO delivery to patients and measured in ppm, mL/breath, mg/breath, mg/kg/hour or any other manner of dosing measurement. The carrier gas may be nitrogen. Embodiments of the present invention also include continuous NO delivery.

In addition, it has been surprisingly found that nasal tolerability of NO was independent of concentration of NO being delivered, but was dependent on dose and dosing rate. Prior to the current application, high concentrations of nitric oxide were considered toxic, especially concentrations above 1,000 ppm. The Occupational Safety and Health Administration (OSHA) has recognized the potential toxicity of nitric oxide and has established a Permissible Exposure Limit (PEL) of 25 ppm. However, unexpectedly this invention describes a method of safely administering nitric oxide at concentrations above 2,000 ppm. This is particularly true if the NO dosing rate is less than or equal to about 166 µg NO/sec.

Before describing several exemplary embodiments of the invention, it is to be understood that the invention is not limited to the details of construction or process steps set forth in the following description. The invention is capable of other embodiments and of being practiced or being carried out in various ways.

As used herein, "cylinder concentration" refers to the concentration of nitric oxide in the therapeutic gas source, which is typically a gas storage cylinder. Cylinder concentrations are typically expressed in parts per million (ppm), with the remainder of the gas in the cylinder comprising a carrier gas such as nitrogen.

"Delivery concentration" refers to the concentration of nitric oxide in the delivery tube immediately prior to the delivery point to the patient, i.e. entering the breathing mask, exiting the nasal cannula, etc. Delivery concentration does not necessarily refer to the alveolar (i.e. lung) concentration, as the delivery concentration may be diluted in the patient's trachea or lungs. "Alveolar concentration" refers to the concentration of nitric oxide in the alveoli or lungs.

According to certain embodiments, the therapeutic gas comprising nitric oxide may undergo dilution in the patient delivery tube due to the presence of other gases entering through the patient end of the patient delivery tube.

In some embodiments, a "cylinder exit concentration" is defined as the concentration of nitric oxide in the therapeutic gas immediately after exiting the gas storage cylinder and entering the patient delivery tube, but prior to any dilution in the patient delivery tube. In other embodiments, a "valve exit concentration" is defined as the concentration of nitric oxide in the therapeutic gas immediately after exiting the control valve, but prior to any dilution in the patient delivery tube.

One aspect of the current invention relates to a method of delivering nitric oxide to a patient comprising administering a dose of nitric oxide having a delivery concentration of greater than 2,000 ppm. In certain embodiments, the delivery concentration is in the range of 2,000 ppm to 30,000 ppm. According to one or more embodiments, the delivery concentration is in the range of 2,000 ppm to 5,000 ppm. In other embodiments, the delivery concentration is greater than 2,200 ppm. Some embodiments provide that the delivery concentration is in the range of 2,200 ppm to 10,000 ppm. In certain embodiments, the delivery concentration is in the range of 2,200 ppm to 5,000 ppm. In a particular embodiment, the delivery concentration is in the range of 2,200 ppm to 2,600 ppm. In another embodiment, the delivery concentration is in the range of 4,000 ppm to 6,000 ppm. According to another embodiment, the delivery concentration is in the range of 4,600 ppm to 5,000 ppm. In some embodiments, the delivery concentration is about 2,440 ppm or about 4,880 ppm.

According to one or more embodiments, the cylinder exit concentration is greater than 2,000 ppm. In certain embodiments, the cylinder exit concentration is in the range of 2,000 ppm to 30,000 ppm. According to one or more embodiments, the cylinder exit concentration is in the range of 2,000 ppm to 5,000 ppm. In other embodiments, the cylinder exit concentration is greater than 2,200 ppm. Some embodiments provide that the cylinder exit concentration is in the range of 2,200 ppm to 10,000 ppm. In certain embodiments, the cylinder exit concentration is in the range of 2,200 ppm to 5,000 ppm. In a particular embodiment, the cylinder exit concentration is in the range of 2,200 ppm to 2,600 ppm. In another embodiment, the cylinder exit concentration is in the range of 4,000 ppm to 6,000 ppm. According to another embodiment, the cylinder exit concentration is in the range of 4,600 ppm to 5,000 ppm. In some embodiments, the cylinder exit concentration is about 2,440 ppm or about 4,880 ppm.

In one or more embodiments, the dose of nitric oxide has a valve exit concentration of greater than 2,000 ppm. In certain embodiments, the valve exit concentration is in the range of 2,000 ppm to 30,000 ppm. According to one or more embodiments, the valve exit concentration is in the range of 2,000 ppm to 5,000 ppm. In other embodiments, the valve exit concentration is greater than 2,200 ppm. Some embodiments provide that the valve exit concentration is in the range of 2,200 ppm to 10,000 ppm. In certain embodiments, the valve exit concentration is in the range of 2,200 ppm to 5,000 ppm. In a particular embodiment, the valve exit concentration is in the range of 2,200 ppm to 2,600 ppm. In another embodiment, the valve exit concentration is in the range of 4,000 ppm to 6,000 ppm. According to another embodiment, the valve exit concentration is in the range of 4,600 ppm to 5,000 ppm. In some embodiments, the valve exit concentration is about 2,440 ppm or about 4,880 ppm.

Any of the methods described herein may limit the dosing rate of nitric oxide to help reduce adverse events such as nasal irritation. As will be explained in more detail in the Examples below, it was surprisingly found that nasal tolerability was dependent on the dosing rate, not the nitric oxide concentration. Accordingly, utilizing specific dosing rates may increase the safety of nitric oxide administration. In various embodiments, the nitric oxide dosing rate may be less than or equal to any of the following rates: 200, 175, 166, 150, 125, 100, 95, 90, 85, 83, 80, 75, 70, 65, 60, 55, or 50 μg NO/sec. The nitric oxide dosing rate is proportional to the concentration of nitric oxide in the therapeutic gas and the flow rate of the therapeutic gas. For example, flowing therapeutic gas at 2 L/min with a nitric oxide concentration of 800 ppm will provide a dosing rate of 33 μg NO/sec. Higher nitric oxide concentrations will require lower therapeutic gas flow rates to be under the threshold for nasal irritation. If the nitric oxide concentration delivered to the patient is greater than 2,000 ppm, then the therapeutic gas flow rate needs to be less than 1 L/min to provide a dosing rate less than 166 μg NO/sec. Accordingly, in some embodiments, the flow rate of therapeutic gas delivered to the patient is less than or equal to the following values: 2, 1.5, 1.25, 1, 0.9, 0.8, 0.7, 0.6, 0.5, 0.45, 0.4, 0.35, 0.3, 0.25, 0.2, 0.15, 0.1 or 0.05 L/min. In a specific embodiment, the delivery concentration is about 4,880 ppm and the dosing rate is less than or equal to about 0.4 L/min. In another specific embodiment, the delivery concentration is about 2,440 ppm and the dosing rate is less than or equal to about 0.8 L/min.

The amount of nitric oxide that is delivered to the patient will depend on many factors. For example, patients that are receiving nitric oxide treatment for various conditions may be prescribed different doses of nitric oxide. Doses that have been reported for use in treating pulmonary arterial hypertension (PAH), chronic obstructive pulmonary disease (COPD), chronic thromboembolic pulmonary hypertension (CTE), idiopathic pulmonary fibrosis (IPF) or pulmonary hypertension (PH), or using nitric oxide as an antimicrobial agent, may be in the range of 0.001 to 4.5 mg/kg/hr. Therefore, in certain embodiments, the dose of nitric oxide is in the range of 0.001 to 4.5 mg/kg/hr. In other embodiments, the dose of nitric oxide is in the range of 0.001 to 0.5 mg/kg/hr.

Also, the dose of nitric oxide may depend on the ideal body weight of the patient. The ideal body weight is related to the lung size of the patient, and will typically be based on the patient's height and gender. As a result, patients with differing lung sizes may be administered different amounts of nitric oxide (in mg/kg/hr or mg/kg/breath).

According to one or more embodiments, the nitric oxide is only delivered during a portion of the patient's breathing cycle. In such embodiments, the nitric oxide is delivered as a pulse instead of a continuous flow of nitric oxide-containing gas. A "pulse," also known as a "bolus" or "plug" or "spike," refers to a single abrupt pulsation or emission of gas. This pulse may be administered during various parts of the patient's breathing cycle. In certain embodiments, the pulse is administered during the first half of inspiration.

In other embodiments, the nitric oxide is delivered continuously to the patient.

FIG. 1 shows an exemplary nitric oxide delivery system 100 for carrying out certain embodiments of the nitric oxide administration method. Gas storage cylinder 103 contains a therapeutic gas comprising nitric oxide, with a cylinder concentration greater than 2,000 ppm. Gas storage cylinder 103 is in fluid communication with patient delivery tube 113, which carries the therapeutic gas from gas storage cylinder 103 to patient breathing mask 111. Control valve 105 regulates the flow of therapeutic gas through patient delivery tube 113. Central processing unit (CPU) 107 is in communication with control valve 105, and CPU 107 sends and receives signals from the control valve 105 to open and close the control valve 105. To deliver a pulse of therapeutic gas, CPU 107 opens control valve 105 to allow therapeutic gas to flow through patient delivery tube 113 to patient breathing mask 111. Control valve 105 is only open for a certain period of time, and the length of the time period will determine the volume of the pulse of therapeutic gas. For example, when control valve 105 is open for a longer period of time, the amount of therapeutic gas in the pulse increases. In certain embodiments, the pulse size may vary from one pulse to the next so that the total amount of therapeutic gas administered over a given time interval is constant, even though a patient's breathing rate may change during this interval.

The pulse of gas comprising nitric oxide may be administered every breath, or it may be administered intermittently. Thus, according to one or more embodiments, the nitric oxide is administered every nth breath, wherein n is 1 or greater. In some embodiments, n is 1, so the pulse is administered to the patient every breath. According to other embodiments, n is greater than 1, thus providing intermittent administration of the dose. For example, when n is 2, the dose is administered every other breath. When the administration is intermittent, n does not need to be a whole number, thus allowing for many possible dosing schedules. For example, when n is 1.5, the dose will be administered 2 out of every 3 breaths.

The CPU 107 may be in communication with a user input device 115. This user input device 115 can receive desired settings from the user, such as the patient's prescription in mg/kg/hr or mg/kg/breath, patient's age, height, sex, weight, etc.

The CPU 107 may also be in communication with a flow sensor (not shown), which would measure the flow of therapeutic gas through control valve 105. The CPU 107 can be coupled to a memory 117 and may be one or more of readily available memory such as random access memory (RAM), read only memory (ROM), flash memory, compact disc, floppy disk, hard disk, or any other form of local or remote digital storage. Support circuits (not shown) can be coupled to the CPU 107 to support the CPU 107 in a conventional manner. These circuits include cache, power supplies, clock circuits, input/output circuitry, subsystems, and the like.

The memory 117 may store a set of machine-executable instructions for calculating the desired volume of the gas pulse and the pulsing schedule to achieve a particular patient prescription. For example, if the patient's breathing rate and the cylinder concentration are known, then the CPU 107 can calculate how much volume of therapeutic gas needs to be administered each breath or set of breaths to provide the desired dosage of nitric oxide. The memory 117 may also record the time that the control valve 105 is open during each pulse, so that future calculations can take into account how much nitric oxide has previously been administered.

When the gas pulse is delivered only during a portion of the patient's breathing cycle, the system further comprises a patient trigger sensor (not shown). The patient trigger sensor can be any suitable pressure sensor. When the patient breathes in during inspiration, it creates a small subatmospheric pressure in the patient delivery tube 113. The patient trigger sensor detects this pressure drop and provides a signal to the CPU 107 that the patient is beginning inspiration. The CPU 107 can then send a signal to the control valve 105 so that the control valve 105 may be opened to deliver the pulse of therapeutic gas.

Similarly, when the patient breathes out, there is a positive pressure in the patient delivery tube 113 and the patient trigger sensor can detect the positive pressure and provide a signal to the CPU 107 indicating the beginning of expiration. As a result, when a patient trigger sensor is used, it is possible for the system to determine the inspiratory and expiratory times in addition to the respiratory rate of the patient.

As the pulse of therapeutic gas contains a high concentration of nitric oxide, the pulse may have a relatively small volume of therapeutic gas and still have the same amount of nitric oxide as a higher volume pulse with a lower concentration of nitric oxide. Therefore, in certain embodiments, the dose of nitric oxide is a small-volume pulse.

According to one or more embodiments, the pulse volume is in the range of 0.001-20 mL. The pulse volume may be as high as 80 mL. Exemplary pulse volumes include about 0.05 mL, about 0.1 mL, about 0.15 mL, about 0.2 mL, about 0.25 mL, about 0.3 mL, about 0.35 mL, about 0.4 mL, about 0.45 mL, about 0.5 mL, about 0.55 mL, about 0.6 mL, about 0.65 mL, about 0.7 mL, about 0.75 mL, about 0.8 mL, about 0.85 mL, about 0.9 mL, about 0.95 mL and about 1 mL.

Certain embodiments provide that the nitric oxide is undiluted before administering to the patient. As shown in FIG. 1, the therapeutic gas can be delivered to patient breathing mask 111 without dilution prior to delivery. Thus, the delivery concentration measured at point 109 is the same as or similar or substantially similar to the cylinder concentration in gas storage cylinder 103. Reference to the delivery concentration and the cylinder concentration being the same concentration means that no inert gas is used to dilute the storage concentration, and the delivery concentration is the same order of magnitude as the storage concentration.

Administering high nitric oxide concentrations allows for the use of smaller gas storage cylinders 103 as the nitric oxide source. For example, a cylinder with about 4,880 ppm of nitric oxide and having a volume of about 0.16 L would generally only need to be changed every 24-96 hours for a 70 kg patient with a prescription of 0.029-0.114 mg/kg/hr. In contrast, the same patient would need to change a 0.16 L cylinder with a concentration of about 800 pm every 4 to 16 hours.

Thus, another aspect of the current invention pertains to administering a dose of nitric oxide from a portable device that comprises a delivery system and a mini-cylinder. As used herein, a "mini-cylinder" is a gas storage cylinder that has a smaller volume and/or lighter weight than a typical cylinder used for delivering nitric oxide. In certain embodiments, a mini-cylinder is a storage cylinder having a volume of less than 2 L or less than 1 L. In other embodiments, a mini-cylinder has a volume less than 0.5 L. According to other embodiments, a mini-cylinder has a volume less than 0.2 L According to one or more embodiments, the mini-cylinder has a volume in the range of 0.01 to 1 L. In certain embodiments, the mini-cylinder has a volume in the range of 0.05 to 0.5 L. In other embodiments, the mini-cylinder has a volume in the range of 0.1 to 0.3 L. In a particular embodiment, the mini-cylinder has a volume in the range of 0.15 to 0.2 L.

In one or more embodiments, the concentration of nitric oxide in the mini-cylinder is greater than 2,000 ppm. In certain embodiments, the mini-cylinder concentration is in the range of 2,000 ppm to 10,000 ppm. According to one or more embodiments, the mini-cylinder concentration is in the range of 2,000 ppm to 5,000 ppm. In other embodiments, the mini-cylinder concentration is greater than 2,200 ppm. Some embodiments provide that the mini-cylinder concentration is in the range of 2,200 ppm to 10,000 ppm. Other embodiments provide that the mini-cylinder concentration is in the range of 2,000 ppm to 5,000 ppm. In a particular embodiment, the mini-cylinder concentration is in the range of 2,200 ppm to 2,600 ppm. In another embodiment, the mini-cylinder concentration is in the range of 4,000 ppm to 6,000 ppm. In a specific embodiment, mini-cylinder concentration is in the range of 4,600 ppm to 5,000 ppm.

A portable device with a mini-cylinder may also be used to provide a pulse of therapeutic gas. Thus, according to one or more embodiments, a portable device administers nitric oxide every nth breath, wherein n is 1 or greater. In some embodiments, n is 1, so the pulse is administered to the patient every breath. According to other embodiments, n is greater than 1, thus providing intermittent administration of the dose.

Another aspect of the current invention provides a method of treating pulmonary hypertension comprising administering a therapeutic gas comprising a dose of nitric oxide having a delivery concentration greater than 2,000 ppm. The therapeutic gas may be administered to the patient from a portable device comprising a delivery system and a mini-cylinder. As with the methods of delivering nitric oxide described above, the delivery concentration, cylinder exit concentration, valve exit concentration, or cylinder concentration of the therapeutic gas used for treating pulmonary hypertension may be within any of the specified ranges.

For treating pulmonary hypertension, the nitric oxide can be administered every nth breath, wherein n is 1 or greater. In certain embodiments, n is 1. In other embodiments, n is greater than 1, thus providing intermittent dosing. Some conditions are treated more effectively with pulsed administration versus continuous administration of therapeutic gas. For example, chronic obstructive pulmonary disease (COPD) is more effectively treated with pulsed administration, and continuous delivery of nitric oxide can actually worsen the symptoms of COPD.

The dose of nitric oxide for treating pulmonary hypertension can be in the range of 0.001 to 4.5 mg/kg/hr. As mentioned above, doses that have been reported for use in treating pulmonary arterial hypertension (PAH), chronic obstructive pulmonary disease (COPD), chronic thromboembolic pulmonary hypertension (CTE), idiopathic pulmonary fibrosis (IPF) or pulmonary hypertension (PH), or using nitric oxide as an antimicrobial agent, may be in the range of 0.001 to 4.5 mg/kg/hr. Therefore, in certain embodiments, the dose of nitric oxide is in the range of 0.001 to 4.5 mg/kg/hr. In other embodiments, the dose of nitric oxide is in the range of 0.001 to 0.5 mg/kg/hr. In certain embodiments, the mini-cylinder used to treat pulmonary hypertension has a volume of less than 1 L. In other embodiments, the mini-cylinder has a volume less than 0.5 L. According to other embodiments, the mini-cylinder has a volume less than 0.2 L According to one or more embodiments, the mini-cylinder has a volume in the range of 0.01 to 1 L. In certain embodiments, the mini-cylinder has a volume in the range of 0.05 to 0.5 L. In other embodiments, the mini-cylinder has a volume in the range of 0.1 to 0.3 L. In a particular embodiment, the mini-cylinder has a volume in the range of 0.15 to 0.2 L.

In one or more embodiments of the method for treating pulmonary hypertension, the therapeutic gas is not diluted prior to administering to the patient. In such embodiments, the delivery concentration is the same as or similar to the cylinder concentration.

EXAMPLES

Example 1: Nasal Tolerability of Nitric Oxide Dosing

A multiple-dose, single-blind, placebo-controlled, tolerance study of pulsed volumes of nitric oxide was completed using healthy subjects. An objective of the study was to determine safe dosing limits of inhaled nitric oxide delivered via a pulse system at cylinder concentrations of 100, 400, and 800 ppm and gas volumes ranging from 4 to 60 mL/breath at dose rates ranging from 17 to 166 μg of NO/sec. Yet another objective of the study was to determine the safety profile, including adverse events (AEs), vital signs and laboratory parameters.

Methodology:

Six subjects were assigned to each cohort (5 NO, 1 placebo) in a randomized, single-blind fashion. All subjects received 72 hours of continuous inhalation. A total of 22 cohorts were evaluated, with NO doses ranging from 125 to 1500 nmol/breath at delivery concentrations of 100, 400, or 800 ppm and varying volumes (4 to 60 mL per breath) in a matrix design, as shown in Table 1. Vital signs and safety laboratory were evaluated. Blood samples for determination of methemoglobin (MetHb) in venous blood, were collected for 72 hours at selected time points.

Number of Subjects:

A total of 132 subjects were enrolled, 131 received treatment (110 NO, 21 placebo) and 129 completed the 72-hour treatment period.

Safety:

Primary safety evaluations included: (1) qualitative assessment of local nasal tolerability via a scoring system (0 to 3); and (2) formation of MetHb (compared with a standard of 7%) following varying concentrations and volumes of pulsed doses of NO. Safety evaluations included assessments of adverse events (AEs), medical history, physical examinations, vital signs, electrocardiograms (ECGs) and laboratory assessments at baseline and during the study period.

Statistical Methods:

All evaluations were performed on the 'Safety' population, defined as all subjects who were enrolled and treated with any amount of study drug. Descriptive statistics included mean, standard deviation (SD), range, median, CV %, geometric mean and geometric CV %.

For analysis purposes, cohorts that received the same dose of NO but different cylinder concentrations and volumes were pooled, thereby creating 15 dose levels (n=14 active NO and 1 placebo, from all dose groups combined). These 15 dose levels were grouped into 4 dose analysis groups: placebo, low-dose NO (1-500 nmol/breath), mid-dose NO (501-1000 nmol/breath), and high-dose NO (1001-1500 nmol/breath).

For analysis purposes, cohorts that received the same dose rate of administration of NO but different cylinder concentrations, doses and volumes were pooled, thereby creating 6

TABLE 1

Group Assignment Matrix

| Dose Level [a] | Cohort | Dose (nmol per breath) | Cylinder Concentration (ppm) | Volume (mL per breath) | Delivery System (High/Low)[b] | Number of Subjects (NO/Placebo)[a] | Dose Rate (μg NO/sec) |
|---|---|---|---|---|---|---|---|
| LOW-DOSE ANALYSIS GROUP | | | | | | | |
| 1 | 1 | 125 | 100 | 30 | High | 5/1 | 21 |
|   | 2 | 125 | 400 | 8  | Low  | 5/1 | 17 |
|   | 3 | 125 | 800 | 4  | Low  | 5/1 | 33 |
| 2 | 4 | 250 | 100 | 60 | High | 5/1 | 21 |
|   | 5 | 250 | 400 | 15 | High | 5/1 | 83 |
| 3 | 6 | 340 | 400 | 20 | High | 5/1 | 83 |
|   | 7 | 340 | 800 | 10 | Low  | 5/1 | 166 |
| 4 | 8 | 420 | 400 | 25 | High | 5/1 | 83 |
| 5 | 9 | 500 | 400 | 30 | High | 5/1 | 83 |
|   | 10| 500 | 800 | 15 | High | 5/1 | 167 |
| MID-DOSE ANALYSIS GROUP | | | | | | | |
| 6 | 11 | 585  | 400 | 35 | High | 5/1 | 83 |
| 7 | 12 | 670  | 400 | 40 | High | 5/1 | 83 |
|   | 13 | 670  | 800 | 20 | High | 5/1 | 167 |
| 8 | 14 | 750  | 400 | 45 | High | 5/1 | 83 |
| 9 | 15 | 840  | 400 | 50 | High | 5/1 | 83 |
|   | 16 | 840  | 800 | 25 | High | 5/1 | 167 |
| 10| 17 | 920  | 400 | 55 | High | 5/1 | 83 |
| 11| 18 | 1000 | 400 | 60 | High | 5/1 | 83 |
|   | 19 | 1000 | 800 | 30 | High | 5/1 | 167 |
| HIGH-DOSE ANALYSIS GROUP | | | | | | | |
| 12| 20 | 1160 | 800 | 35 | High | 5/1 | 167 |
| 13| 21 | 1340 | 800 | 40 | High | 5/0[c] | 167 |
| 14| 22 | 1500 | 800 | 45 | High | 5/1 | 167 |

[a] For analysis purposes, placebo-treated subjects from all cohorts were combined into a single dose level [15th] and 1 dose analysis group.
[b] Low-dose system delivered volumes ranging from 3 mL through 10 mL per pulse at a flow rate of 2 L/min; High-dose system delivered volumes ranging from 15 mL through 60 mL at a flow rate of 10 L/min.
[c] One subject in cohort 21 did not receive placebo due to a limitation in supplies.

dose rate of administration levels (n=5 active NO and 1 placebo, from all rate of administration groups combined). The dose rate of administration of NO was calculated as the product of the flow rate of NO and the cylinder NO concentration.

Adverse Events:

The overall incidence of AEs was only dose related. Table 2 below shows that the most frequently occurring AEs, including headache, back pain, and nausea.

TABLE 2

Most Frequently Occurring Adverse Events
(% of subjects at each dose level)

| Preferred Term | Placebo (N = 21) | NO 1-500 nmol/breath (N = 50) | NO 501-1000 nmol/breath (N = 45) | NO 1001-1500 nmol/breath (N = 15) |
|---|---|---|---|---|
| Total % with any AE | 28.6 | 28.0 | 33.3 | 53.3 |
| Headache | 4.8 | 8.0 | 4.4 | 20.0 |
| Back pain | 0.0 | 6.0 | 4.4 | 0.0 |
| Nausea | 0.0 | 2.0 | 4.4 | 6.7 |

One subject (6.7%) in the high-dose NO group withdrew due to chest discomfort, decreased $O_2$ saturation, and dyspnea.

Nasal Tolerability:

Analysis for nasal tolerability at 72 hours by individual NO dose group, pulse volume of carrier airflow, and NO cylinder concentration demonstrates that the nasal tolerability was related to the dose levels and NO flow rate used in the trial as there was no correlation with either pulse volume or cylinder concentration. A multivariate analysis, with tolerability score as the response variable and with dose level, cylinder concentration and pulse volume as the covariates, demonstrated that the NO dose level was the only significant covariate (p=0.006). The cylinder concentration (p=0.525) and the pulse volume (p=0.077) were not significant; however the tolerability was affected by NO dosing rate. Nasal tolerability at dosing rates up to 166 µg/sec were not different from placebo; a dosing rate of 166 µg g/sec was associated with a higher incidence of nasal irritation, including a case of nasal ulceration. Therefore, the nasal tolerability after 72 hours of pulsed dosing of NO is related to the NO dose and the dosing rate and not to either the pulsed volume of carrier airflow or the NO cylinder concentration. Tables 3, 4 5 and 6 show the local tolerability analysis based on dose level, cylinder concentration, pulse volume and dosing rate, respectively.

Furthermore, at clinical doses less than 420 nmol/breath (about 0.4 mg/kg/hr in an average 70 kg adult with a respiratory rate of 12 breaths/min), there was no evidence of nasal irritation with 48 hours of continuous administration of NO and at 72 hours the nasal tolerability is no different than for placebo (3/18 placebo subjects with nasal redness vs. 2/18 NO subjects with nasal redness).

TABLE 3

Local Tolerability Analysis at 72 Hours by Dose Group

| Dose Group (nmol/breath) | Mean Score | P-value[1] |
|---|---|---|
| Placebo | 0.14 | 0.006 |
| 125 | 0.07 | |
| 250 | 0.00 | |
| 340 | 0.10 | |
| 420 | 0.00 | |
| 500 | 0.10 | |

TABLE 3-continued

Local Tolerability Analysis at 72 Hours by Dose Group

| Dose Group (nmol/breath) | Mean Score | P-value[1] |
|---|---|---|
| 585 | 0.40 | |
| 670 | 0.00 | |
| 750 | 0.00 | |
| 840 | 0.60 | |
| 920 | 0.00 | |
| 1000 | 0.33 | |
| 1160 | 0.40 | |
| 1340 | 0.20 | |
| 1500 | 0.75 | |

[1]Obtained from a multivariate analysis with tolerability score as the response variable and dose, cylinder concentration, and pulse volume as the covariates.

TABLE 4

Local Tolerability Analysis at 72 Hours by Cylinder Concentration

| Cylinder Concentration (ppm) | Mean Score | P-value[1] |
|---|---|---|
| 0 | 0.14 | 0.525 |
| 100 | 0.10 | |
| 400 | 0.09 | |
| 800 | 0.33 | |

[1]Obtained from a multivariate analysis with tolerability score as the response variable and dose, cylinder concentration, and pulse volume as the covariates.

TABLE 5

Local Tolerability Analysis at 72 Hours by Pulse Volume

| Pulse Volume (mL/pulse) | Mean Score | P-value[1] |
|---|---|---|
| 0 | 0.14 | 0.077 |
| 4 | 0.00 | |
| 8 | 0.00 | |
| 10 | 0.20 | |
| 15 | 0.10 | |
| 20 | 0.00 | |
| 25 | 0.60 | |
| 30 | 0.07 | |
| 35 | 0.40 | |
| 40 | 0.10 | |
| 45 | 0.33 | |
| 50 | 0.00 | |
| 55 | 0.00 | |
| 60 | 0.30 | |

[1]Obtained from a multivariate analysis with tolerability score as the response variable and dose, cylinder concentration, and pulse volume as the covariates.

TABLE 6

Local Tolerability Analysis at 72 Hours by NO Dosing Rate

| Dosing Rate of NO (µg NO/sec) | Percent of Subjects Experiencing Nasal Irritation |
|---|---|
| 0 | 14.3% |
| 17 | 0% |
| 21 | 10.0% |
| 33 | 10% |
| 83 | 10% |
| 167 | 36.4% |

Example 2: Administration of High Doses of Nitric Oxide

In this prophetic example, patients are administered a dose of nitric oxide during inspiration, the dose comprising a delivery concentration of greater than 2,000 ppm. Some patients are administered a dose of nitric oxide in the range of 2,200 to 2,600 ppm, such as about 2,440 ppm nitric oxide. Other patients are administered a dose of nitric oxide in the range of 4,400 to 5,000 ppm nitric oxide, such as about 4,880 ppm nitric oxide. Other patients may be administered doses above 5,000 ppm, including up to about 20,000 ppm nitric oxide.

The patients are administered a pulse of therapeutic gas comprising nitric oxide every nth breath, with n being greater than or equal to 1. For one group of patients, n is equal to one such that the pulse of therapeutic gas is administered every breath. For another group of patients, n is greater than 1 such that the pulse of therapeutic gas is administered intermittently.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of treating pulmonary hypertension, the method comprising administering a dose of nitric oxide (NO) to a patient in need thereof, the dose comprising a delivery concentration of greater than 2,000 ppm NO and being administered at a dosing rate less than or equal to 166 µg NO per second.

2. The method of claim 1, wherein the delivery concentration is in the range from greater than 2,000 ppm to 20,000 ppm.

3. The method of claim 1, wherein the delivery concentration is in the range from 2,200 ppm to 5,000 ppm.

4. The method of claim 1, wherein the dose is in the range from 0.001 to 4.5 mg NO/kg/hr.

5. The method of claim 1, wherein the dose is administered every breath.

6. The method of claim 1, wherein the dose is administered intermittently.

7. The method of claim 1, wherein the nitric oxide is administered in undiluted form such that the delivery concentration is the same as a storage concentration.

8. The method of claim 1, wherein the dosing rate is less than or equal to 100 µg NO per second.

9. The method of claim 1, wherein the dosing rate is less than or equal to 83 µg NO per second.

10. The method of claim 1, wherein the pulmonary hypertension is pulmonary arterial hypertension (PAH).

11. The method of claim 1, wherein the pulmonary hypertension is associated with chronic obstructive pulmonary disease (COPD).

12. A method of reducing nasal irritation during nitric oxide administration, the method comprising administering a therapeutic gas comprising nitric oxide (NO) to a patient, wherein the therapeutic gas is administered to the patient at a delivery concentration of greater than 2,000 ppm NO and at a dosing rate less than or equal to 166 µg NO per second.

13. The method of claim 12, wherein the delivery concentration is in the range from greater than 2,000 ppm to 20,000 ppm.

14. The method of claim 12, wherein the delivery concentration is in the range from 2,200 ppm to 5,000 ppm.

15. The method of claim 12, wherein the patient is administered therapeutic gas at a dose of 0.001 to 4.5 mg NO/kg/hr.

16. The method of claim 12, wherein the therapeutic gas is administered every breath.

17. The method of claim 12, wherein the therapeutic gas is administered intermittently.

18. The method of claim 12, wherein the dosing rate is less than or equal to 100 µg NO per second.

19. The method of claim 12, wherein the dosing rate is less than or equal to 83 µg NO per second.

20. The method of claim 12, wherein the patient is diagnosed with pulmonary arterial hypertension (PAH) or chronic obstructive pulmonary disease (COPD).

* * * * *